(12) United States Patent
Hajianpour

(10) Patent No.: US 6,406,454 B1
(45) Date of Patent: Jun. 18, 2002

(54) SURGICAL SUCTION PROBE SYSTEM WITH AN EASILY CLEANED INTERNAL FILTER

(76) Inventor: Mohammed Ali Hajianpour, 1706 Vestal Dr., Coral Springs, FL (US) 33071

( * ) Notice: Subject to any disclaimer, the term of this patent is extended or adjusted under 35 U.S.C. 154(b) by 0 days.

(21) Appl. No.: 09/524,792

(22) Filed: Mar. 14, 2000

(51) Int. Cl.[7] ............................................. A61M 31/00
(52) U.S. Cl. ......................... 604/48; 604/902; 210/106
(58) Field of Search ..................... 604/48, 902; 210/106

(56) References Cited

U.S. PATENT DOCUMENTS

| | | | | |
|---|---|---|---|---|
| 3,623,607 | A | * 11/1971 | Loos | 210/106 |
| 3,785,380 | A | * 1/1974 | Brumfield | 604/119 |
| 3,863,624 | A | * 2/1975 | Gram | 600/571 |
| 3,889,657 | A | * 6/1975 | Baumgarten | 600/571 |
| 3,890,712 | A | * 6/1975 | Lopez | 433/92 |
| 4,068,664 | A | 1/1978 | Sharp et al. | 128/276 |
| 4,417,874 | A | 11/1983 | Andersson et al. | 433/96 |
| 4,468,217 | A | 8/1984 | Kuzmick et al. | 604/48 |
| 4,701,164 | A | 10/1987 | Cassou et al. | 604/218 |
| 4,813,926 | A | 3/1989 | Kerwin | 604/118 |
| 4,878,900 | A | 11/1989 | Sundt | 604/119 |
| 4,886,492 | A | * 12/1989 | Brooke | 604/49 |
| 5,013,300 | A | 5/1991 | Williams | 604/119 |
| 5,078,605 | A | 1/1992 | Sutter et al. | 433/165 |
| 5,098,416 | A | 3/1992 | Imonti | 604/319 |
| 5,123,840 | A | 6/1992 | Nates | 433/95 |
| 5,244,458 | A | 9/1993 | Takasu | 604/22 |
| D365,146 | S | 12/1995 | Olson | D24/108 |
| 5,520,668 | A | 5/1996 | Greff et al. | 604/321 |
| 5,597,385 | A | 1/1997 | Moerke | 55/274 |
| 5,630,939 | A | 5/1997 | Bulard et al. | 210/416.1 |
| 5,741,134 | A | 4/1998 | Davis | 433/91 |
| 5,766,134 | A | 6/1998 | Lisak et al. | 600/562 |
| 5,779,649 | A | 7/1998 | Herbert | 600/571 |
| 5,807,353 | A | 9/1998 | Schmitz | 604/264 |
| 6,083,175 | A | * 7/2000 | Lundgren | 600/562 |

* cited by examiner

Primary Examiner—John Fox
(74) Attorney, Agent, or Firm—Ronald V. Davidge

(57) ABSTRACT

A suction probe system for cleaning debris from a surgical site includes a probe tip, a filter unit in fluid communication with the probe tip, and a suction source in fluid communication with the filter unit. The filter unit includes a cylindrical filter having an inner chamber attached to the suction source and an outer surface which accumulates debris particles too large to pass through holes within the cylindrical filter. The filter unit also includes a slider having an open-ended cylinder which is slid along the outside of the cylindrical filter to remove accumulated debris particles and to push these debris particles into a reservoir within the filter unit. The slider and the probe tip can be made integral parts of a single sliding member.

16 Claims, 2 Drawing Sheets

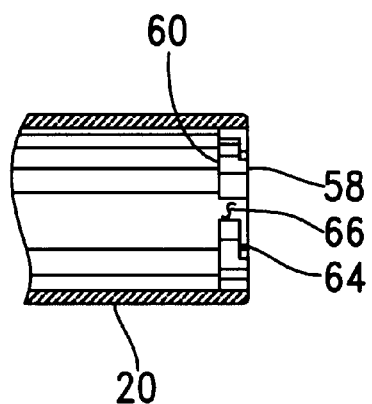
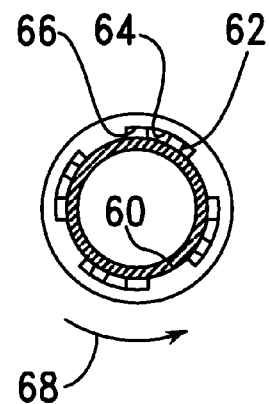
FIG. 3  FIG. 4
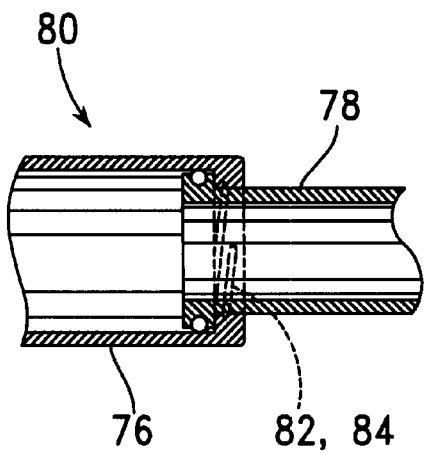
FIG. 5
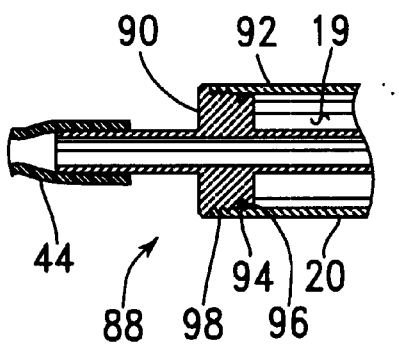
FIG. 6

SURGICAL SUCTION PROBE SYSTEM WITH AN EASILY CLEANED INTERNAL FILTER

BACKGROUND INFORMATION

1. Field of Invention

This invention relates to a probe forming a part of a surgical suction system for the removal of debris from a surgical site, and, more particularly, to such a probe including an internal filter for removing and holding larger pieces of such debris from waste slurry flowing through the probe.

2. Description of the Related Art

The patent literature describes a number of suction probes for use in surgical suction systems to remove debris from a surgical site, with the probe including or being associated with an internal filter for removing and holding the larger pieces of waste slurry flowing through the probe. Such a suction probe has an inlet large enough to permit the entrance of debris particles too large to be handled reliably through the remaining portion of the suction system, such as the conduit leading to a suction source. These particles are trapped within the internal filter. Each such suction probe is separable into two pieces so that the internal filter can be cleaned or replaced as it becomes clogged or as tissue samples are needed, for example, for pathology.

For example, U.S. Pat. No. 4,468,217 to Kuzmick et al. describes a surgical suction tip including an inner removable filter device. The housing includes a suction opening at one end and a filter receiving handle formed as a sleeve at the other end; the inner removable filter device is connected in the filter receiving handle by a quick connect-disconnect means; the housing tapers to increase in size from its suction opening to the filter device. A seal is located between the housing and the filter device. Within this device, filtration occurs through a cylindrical filter having a number of holes between a chamber within the cylindrical filter and a chamber within the device but outside the cylindrical filter. The chamber within the cylindrical chamber is in fluid communication with a suction source, while the chamber outside the cylindrical chamber is in fluid communication with an aperture at the distal end of the probe tip, through which debris is sucked.

U.S. Pat. No. 5,779,649 to Herbert describes a surgical suction wand comprising a generally tubular body with a hollow tip at one end thereof, a cap releasably closing the other end of the tubular body, and a filter member within the body and joinable to the under surface of the cap. The filter member is wedge-shaped, having a number of holes through which debris is sucked into a space within the filter. The filter member is removed, along with the cap, and is cleaned and returned to the interior of the tubular body as required. The cap snaps in place on the tubular body, with a ridge extending around an end of the tubular body snapping in place within a groove extending around an end of the cap, and with a tab being provided to ease the disengagement of the snap fit.

U.S. Pat. No. 5,630,939 to Bulard et al. describes a filter assembly for elective use in conjunction with a surgical evacuation system. The filter assembly includes a filter housing having a head portion and a body portion with a through passageway extending therebetween defining a filter receiving chamber. The head portion is connectable to an aspirator tip and the body portion is connectable to a flexible suction conduit. A filter element is disposed within the filter receiving chamber of the filter housing. The filter element includes a head member having a fluid flow passageway extending therethrough, a fluid impermeable base member spatially disposed from the head member, and a fluid permeable body member disposed between the head member. The head member and the body member are joined by a cylindrical surface having an O-ring seal, so that the head member and the body member are separated by twisting and sliding to install, remove, or replace the filter element.

U.S. Pat. No. 5,766,134 to Lisak et al. describes a collector unit for collecting tissue or bone from a dental patient during a dental implant procedure. The collector unit includes a cover member, a filter support member, a filter medium, and a gasket support member. The support member is mountable within the cover member with the gasket member positioned therebetween to form the unit. The support member has a pair of spaced-apart, opposed filter support arms for removably supporting a substantially flat section of filter medium, so that the filter medium overlays an input passageway through which liquid is drawn. After the unit is disassembled, the filter medium is removable from the supporting structure so that it can be positioned in a flat orientation to facilitate the removal of bone or tissue specimens therefrom. Once removed, the filter medium cannot be reattached to the supporting structure.

U.S. Pat. No. 5,807,353 to Schmitz describes an aspiration device for separating liquid content of a body fluid and irrigation fluid, if any, from solid material. The device includes an integrally formed housing and an integrally formed separating element, which is detachably interconnectable to the housing. The housing includes a proximal segment for defining a hollow space to receive part of the separating element. The separating element includes a filter element for separating the liquid content of the body fluid from the solid matter and for collecting the solid matter in the interior of the filter element. The separating element further includes an end connector for interlocking the separating element with the housing, and an egress tube for conveying the liquid content outside the aspiration device. The filter element is a slotted cylinder, with debris being sucked through and end of the cylinder, and with liquid being further sucked outward through the slots while solid material remains within the cylinder. The device is cleaned, or collected material is removed, by twisting a threaded end connector so that it is disengaged from the proximal end of the housing. The separating element is then removed, so that the filter can be cleaned or replaced.

Each of the patents described above discloses a suction device having an internal filter which can be cleaned or removed and replaced only when the suction device is taken apart to reveal the internal filter. What is needed is a method providing for cleaning the filter without disassembling the device and without a need to wipe the filter. The process of disassembly, wiping, and reassembly is relatively time consuming, and must often be performed several times during a surgical procedure. This process results in a number of pieces of the suction device and the filter, which must be separately handled and reassembled. A lack of the suction process during this process can also interrupt other surgical procedures taking place. Furthermore, what is needed is an ability to hold trapped debris so that it is unnecessary to handle such debris during a surgical procedure.

A number of U.S. patents describe surgical suction probes without internal filters. For such a device to be used reliably to remove debris from a surgical site, solid fragments the tip aperture must be small enough to prevent the aspiration of particles from the waste slurry which are large enough to clog the conduit extending between the suction probe and a vacuum source generating the suction, the vacuum source itself, or a fluid separation device associated with the vacuum source. On the other hand, fragments too large to pass through the aperture may be held externally at the aperture or allowed to fall back into the surgical site. What is needed is a mechanism allowing such fragments to be trapped and held within the suction probe, without being allowed to flow along the conduit to the vacuum source, and without being redeposited at the surgical site. This need is apparent when the suction probe is used to clean debris from the site of an orthopaedic procedure, in which bone fragments of various sizes are produced.

Examples of such patents include U.S. Pat. No. 5,520,668 to Greff et al., which describes a surgical suction system and method including a source of suction and a conduit having a distal end and a proximal end. At its distal end, the conduit has a diameter not greater than about 5/8 inch to provide limited access to the surgical site and an inside diameter not less that about 1/4 inch to accommodate the bone fragments in the waste slurry. A coupling is provided for connecting the proximal end of the conduit to the suction source in order to provide suction at the distal end of the conduit at a velocity not less than about ninety miles an hour. A fluid containment vessel can be connected between the conduit and the source of suction to provide a liquid trap for the waste slurry passing along the conduit.

U.S. Pat. No. 4,878,900 to Sundt describes a probe and suction device for use during surgery, including an elongated tubular handle adapted for connection to a source of suction and a separable elongated tubular probe and suction member. It includes a suction regulating orifice in the handle and is characterized by a positive snap-on rotatable connection between the handle and the probe and suction member. The distal end of the probe and suction member is blunted to avoid tissue damage.

U.S. Pat. No. 5,123,840 to Nates describes a suction probe including a controllable suction port, which the individual using the probe can partly or totally cover with a finger to control the level of suction available at the probe tip, through which debris is removed.

U.S. Pat. No. 4,068,664 to Sharp et al. describes a surgical suction wand assembly including a modular suction wand having a hollow suction tip, along which a number of laterally disposed external apertures extend. The tip may be provided with an elongated interiorly disposed tube simultaneously providing for effective aspiration of small amounts of liquid as well as a large suction area for efficiently aspirating larger volumes with minimal opportunity for obstruction. While the apertures in the suction tip provide a filter preventing the aspiration of larger fragments, such fragments may be expected either to remain held in place externally on the suction tip as it is used, or to fall back into the surgical site. Thus, what is needed is a mechanism for removing such fragments from these apertures and for safely holding them as the surgical wand is used.

SUMMARY OF THE INVENTION

It is therefore a first objective of the present invention to provide a surgical suction probe having an internal filter which can be cleaned without disassembling the suction probe.

It is a second objective of the present invention to provide a surgical suction probe having an internal reservoir for holding debris cleaned from an internal filter.

According to a first aspect of the present invention, there is provided apparatus for removing debris from a surgical site. The apparatus includes a hollow probe tip, a filter chamber, and a slider. The hollow probe tip includes a tip aperture and an internal passageway extending from the tip aperture. The filter chamber includes a reservoir, an output port connectable to a suction source, and a filter surface, with the first side of the filter surface being in fluid communication with a passage, within the hollow probe tip, and with a second side of the filter surface in fluid communication with the internal passageway of the hollow probe tip. The slider is movable within the filter chamber, with movement of the slider within the filter chamber in a first direction pushing debris within the filter chamber from the first side of the filter surface into the reservoir.

BRIEF DESCRIPTION OF THE DRAWINGS

FIG. 3 is a fragmentary cross-sectional view of a filter section in of the probe of FIG. 2, showing internal features used fort he attachment of a distal section of the probe to the filter section;

FIG. 4 is a transverse cross-sectional view of the surgical suction probe of FIG. 1, taken as indicated by section lines IV—IV in FIG. 2;

FIG. 5 is a fragmentary longitudinal cross-sectional view of a distal end of a filter housing in engagement with a proximal end of a slider, made in accordance with a third embodiment 80 of the present invention;

FIG. 6 is a fragmentary longitudinal cross-sectional view of a proximal end of a filter housing made in accordance with a fourth embodiment of the present invention.

DESCRIPTION OF THE INVENTION

Figure 1:
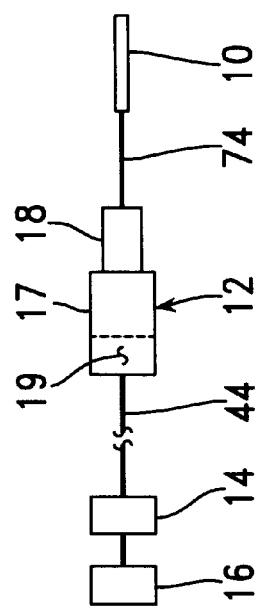
FIG. 1 is a schematic view of a surgical suction system built in accordance with the present invention.

FIG. 1 is a schematic view of a surgical suction system built in accordance with the present invention for removing debris from a surgical site, including a probe tip 10, a first filter 12, a second filter 14, and a vacuum source 16. The surgical suction system may be partly composed of a central vacuum system within the hospital, with the probe tip 10 and the first filter 12 being disposed within an operating room, and with the second filter 14 and the vacuum source 16 being disposed in another part of the hospital in the form of a central vacuum system. In accordance with the present invention, the first filter 12 includes a filter section 17, a slider 18, and a reservoir 19. When the slider 18 is moved into the filter section 16, debris held on a surface of a filter surface (not shown) within the filter section 17 is scraped off the filter surface and deposited within the reservoir 19.

Figure 2:
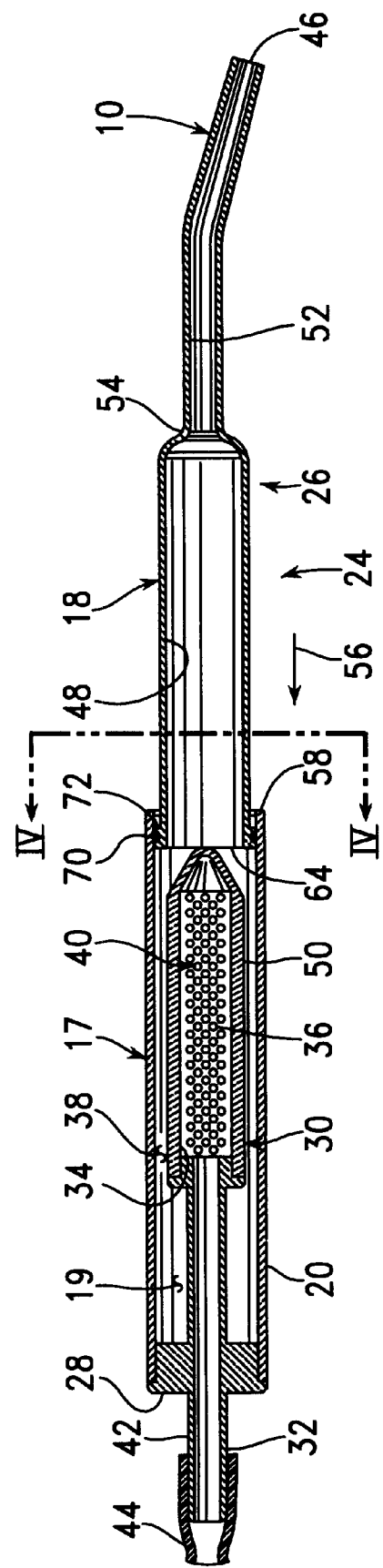
FIG. 2 is longitudinal cross-sectional view of a first embodiment of a surgical suction probe built in accordance with the present invention for use as a part of the system of FIG. 1.

FIG. 2 is a longitudinal cross-sectional view of a surgical suction probe 24 built in accordance with a first embodiment of the present invention. In this embodiment, the slider 18 and the probe tip 10 are configured as integral parts of a sliding member 26. The filter section 17 includes a housing 20 with the reservoir 19 near a proximal end 28 of the filter section 17, a cylindrical filter 30, and a hollow tube 32 extending through the proximal end 28 in communication with a chamber 34 within the cylindrical filter 30. The cylindrical filter 30 includes a number of holes 36, extending between the chamber 34 within the filter 30 and a chamber 38 within the housing 19. Preferably, the filter holes 36 extend in a hole pattern 40 along each of two diametrically opposed sides of the cylindrical filter 30, with the individual holes 36 being aligned in a common direction, facilitating the manufacture of the cylindrical filter 30 by a thermoplastic molding process.

To use the surgical suction probe 24 to remove debris from a surgical site, the external end 42 of the hollow tube 32 is connected to a vacuum system by means of a flexible hose 44. The probe tip 10 is then placed within the surgical site so that debris is sucked inward through a tip aperture 46 at the distal end of the probe tip 10. The debris is pulled through the hollow probe tip 10 and through a chamber 48 within the slider 18. The debris is then pulled into the chamber 38 within the filter section 17. The portions of the debris which can pass through the filter holes 36 enter the chamber 34 within the cylinder filter 30, while particles which are too big to pass through the filter holes 36 remain within the chamber 38, generally being held within the annular region 50 within the chamber 38 outwardly adjacent the cylindrical filter 30.

The tip aperture 46 is preferably substantially larger in diameter than each of the individual filter holes 36, so that debris particles within a range of sizes, having been drawn into the suction probe 10, are not allowed to pass through this probe 10 into the hollow tube 32 and thereafter into the flexible hose 44 (shown in FIG. 1) to the associated vacuum system. Also, the individual filter holes 36 are preferably substantially smaller in diameter than the hollow tube 32. These conditions are met, for example, with a tip aperture 46 having a diameter of 4.8 mm (0.188 inch), individual filter holes 36 having diameters of 1.9 mm (0.073 inch), and a hollow tube 32 having an internal diameter of 6.4 mm (0.250 inch). Furthermore, to prevent debris from being trapped within the probe tip 10, the tip aperture 46 is preferably the smallest part of the opening 52 extending through the probe tip. For example, this opening 52 may be tapered from the tip aperture 46, having a diameter of 4.8 mm (0.118 inch) to an opening at the proximal end 54 of the probe tip 10 having a diameter of 6.4 mm (0.250 inch).

The suction probe 24 can be used in this way to remove debris until debris accumulates within the annular region 50 outwardly adjacent the cylindrical filter 30 to an extent sufficient to substantially block the flow of material into the cylindrical filter 30. As this occurs, the efficiency of the suction probe 24 declines to a noticeable extend, and the probe is removed from the surgical site so that debris can be cleared from the annular region 50 by manually moving the slider 18 in the direction of arrow 18 in the direction of arrow 56, with the slider 18 moving into the annular region 50. This movement pushes debris held within the annular region 50 into the reservoir 19 forming a proximal portion of the chamber 38 within the filter section 17. Thus, with the housing 20, the slider 18, and the cylindrical filter 30 being aligned coaxially, the annular region 50 is cleared with a single movement of the slider 18. After debris is cleared in this way, the slider is manually returned to its initial position, opposite the direction of arrow 56, and the process of removing debris from the surgical site is continued.

This method for cleaning debris from the annular region 50 is practical because the suction probe 24 is disposable, being discarded after use on a single patient or on a single surgical site. Thus, the reservoir 19 can be configured to be of adequate size to avoid overfilling before the suction probe 24 is discarded. Typically, the suction probe 24 aspirates a mixture of air, liquid, and particles such as bone fragments and pieces of bone cement. This mixture does not fill the chamber 38 with liquid, so the slide 18 can be moved in the direction of arrow 56 while compressing air within the chamber 38 and while forcing a slurry of small particles and liquid into filter holes 36 which have not become totally clogged.

FIGS. 3 and 4 show a mechanism for controlling movement of the slider 18 into the filter chamber 38. This type of control is needed to allow the suction probe 24 to be operated as described above; without a mechanism to hold the slider 18 in its extended position, as shown in FIG. 2, the slider 18 would be pulled inward, in the direction of arrow 56 by suction established within the filter section chamber 38. FIG. 3 is a fragmentary longitudinal cross-sectional view of the distal end 58 of the filter housing 20, particularly showing locking segments 60 extending radially inward, while FIG. 4 is a transverse cross-sectional view of the suction probe 24, taken as indicated by section lines IV—IV in FIG. 2.

The slider 18 includes four integral locking tabs 62, extending outward from its proximal end 64 in a cruciform pattern. During the cleaning of debris from a surgical site, these four locking tabs 62 are held within four corresponding circumferential grooves 64, each of which extends partly around a locking segment 60 at the distal end 58 of the filter housing 20. A groove 66 extends between each pair of adjacent locking segments 60, providing four grooves 66 in a cruciform pattern. Thus, when it is determined that the annular region 50 outwardly adjacent the cylindrical filter 30 is to be cleaned, the suction probe 24 is removed from the surgical site, and the slider 18 is rotated in the counterclockwise direction of arrow 68 relative to the filter section 17. Such rotation ends with the four locking tabs 62 aligned with the four corresponding grooves 68, in a relationship allowing the slider 18 to be moved in the direction of arrow 56 into the chamber 38 within the filter section 17.

After the annular region 50 is cleaned by moving the slider 18 into the chamber 38, the slider 18 is pulled outward, opposite the direction of arrow 56, and is rotated as needed to align the locking tabs 62 with the grooves 68. When this alignment occurs, the slider 18 is pulled outward into the fully extended position in which it is shown in FIG. 2. The slider 18 is then rotated opposite the direction of arrow 68 relative to the filter section 17, locking the slider 18 in place in its fully extended position, and the probe tip 10 is returned to the surgical site to continue the suction process.

A sliding seal is maintained between the proximal end 64 of the slider 18 and the internal surface of the filter housing 20 by means of an O-ring seal 70 held within a grooved seal holder 72 of the slider 18. This outward-extending seal holder 72 also contacts the inward-extending locking segments 60 of the filter housing 20, preventing the slider 18 from being separated from the filter housing as the slider 18 is pulled opposite the direction of arrow 56.

The filter housing 20 and various other members of the suction probe 24 are preferably composed of a transparent material, such as a transparent form of polycarbonate, so that material clogging the filter can be easily observed.

Referring again to FIG. 1, a surgical suction probe built in accordance with a second embodiment of the present invention includes a first filter 12 which is separate from the probe tip 10, but which includes a slider 18 and a reservoir 19 operating as described above relative to the first embodiment 24. The first filter 12 and the probe tip 10 are separated by a flexible hose 74, through which debris is drawn. Thus, the flexible hose 74 of FIG. 1 is optional, only being used as a part of a second embodiment of the suction probe.

FIG. 5 is a fragmentary longitudinal cross-sectional view of a distal end of a filter housing 76 in engagement with a proximal end of a slider 78, with both the filter housing 76 and the slider 78 being made in accordance with a third embodiment 80 of the present invention. The filter housing 76 includes an internal thread 82, while the slider 78 includes an external thread 84, forming an alternative arrangement for locking the slider 78 in place on the filter housing 76 during the use of the suction probe 80 to remove debris from a surgical site. Each of the threads 82, 84 may be a single thread, extending partly or fully around the circumference of a threaded surface, or there may be two or more threads on the housing 76 and the slider 78, spaced apart from one another to extend in an intertwined manner or limited in length to separate portions of the circumference of the threaded surface. An advantage of using multiple threads arises from the fact that multiple angular positions are available for starting the process of screwing the slider 78 into a locked condition on the filter housing 76. An advantage of this third embodiment 80 over the first embodiment 24, discussed above in reference to FIGS. 2–4, arises from the ease with which such threads are engaged, compared with a need, in the first embodiment 24, to align the locking tabs 62 with the grooves 66, before the slider 18 can be moved opposite the direction of arrow 56 into a locked condition. Other aspects of the filter housing 76 and the slider 78 are the same as those of the corresponding filter housing 76 and the slider 18 of the first embodiment 24.

Referring to FIGS. 1 and 5, during the process of assembling the first embodiment 24 of the suction probe the various elements are joined in a manner allowing the slider 18 to be moved in the direction of arrow 56 and opposite thereto, but so that it cannot be separated from the remaining parts of the suction probe. The distal end 28 is permanently attached within the filter housing 17, for example, by an adhesive. The grooved seal holder 72 prevents separation of the slider 18 in the direction of arrow 56 from the filter housing 17. The debris trapped in the reservoir 19 remains there as the suction probe 24 is disposed. Similar conditions occur in the third embodiment 80 of the suction probe, with the slider 78 being trapped to slide within the filter housing 76, and with debris being trapped in the reservoir. In many applications, this is advantage, providing for the containment of potentially dangerous waste.

In some applications, there is a need to remove and save the debris stored in the reservoir 19, for example, for examination by a pathologist. Therefore, FIG. 6 is a fragmentary longitudinal cross-sectional view of the proximal end of a fourth embodiment 88 of the suction probe, which is configured so that the distal end 90 may be removed from the filter housing 92, providing for the removal of debris from the reservoir 19. An O-ring 94 in a groove 96 within the distal end 90 forms a seal between the distal end 90 and the filter housing 92. The distal end 90 and the filter housing 92 are also provided with mating threads 98, which hold the distal end 90 attached to the filter housing 92. The contents of the reservoir 19 are emptied after the distal end 92 is unscrewed from the filter housing 92.

While the present invention has been described in its preferred forms of embodiments with some degree of particularity, it is understood that this description has been given only by way of example and that numerous changes in the details of construction, fabrication, and use, including changes in the combination and arrangement of parts, may be made without departing from the spirit and scope of the invention.

I claim:

1. Apparatus for removing debris from a surgical site, wherein said apparatus comprises:
    a hollow probe tip including a tip aperture and an internal passageway extending from said tip aperture;
    a filter housing including a reservoir, an output port connectable to a suction source, and a filter surface, wherein said filter surface includes a plurality of filter holes, wherein a first side of said filter surface is in fluid communication with said internal passageway of said hollow probe tip, and wherein a second side of said filter surface is in fluid communication with said output port of said filter housing; and
    a slider movable within said filter housing, wherein movement of said slider within said filter housing in a first direction pushes debris within said filter housing from said first side of said filter surface into said reservoir.

2. The apparatus of claim 1, wherein
    said filter surface is cylindrical,
    said first side of said filter surface is outside said filter surface, and
    said slider includes a cylindrical surface coaxially aligned with said filter surface, open at a first end, and movable in said first direction over said filter surface.

3. The apparatus of claim 2, wherein
    said filter housing is cylindrical and coaxially aligned with said filter surface, and
    moving said slider in said first direction clears debris from an annular region around said filter housing.

4. The apparatus of claim 3, wherein an outer surface of said slider includes a seal wiping on an inner surface of said filter housing.

5. The apparatus of claim 3, wherein said filter housing is composed of a transparent material.

6. The apparatus of claim 1, wherein said slider and said hollow probe tip form integral portions of a sliding member.

7. The apparatus of claim 6, wherein
    said filter surface is cylindrical,
    said first side of said filter surface is outside said filter surface, and p1 said slider includes a cylindrical surface coaxially aligned with said filter surface, open at a first end, and movable in said first direction over said filter surface.

8. The apparatus of claim 7, wherein
    said filter housing is cylindrical and coaxially aligned with said filter surface, and
    moving said slider in said first direction clears debris from an annular region around said filter housing.

9. The apparatus of claim 8, wherein an outer surface of said slider includes a seal wiping on an inner surface of said a housing surrounding said filter housing.

10. The apparatus of claim 8, wherein said filter housing and said probe tip are composed of transparent material.

11. The apparatus of claim 1, additionally comprising locking means for holding said slider to said filter housing in a position of maximum extension of said slider from said filter housing.

12. The apparatus of claim 11, wherein said filter housing is cylindrical, and wherein said locking means includes:
    a plurality of tabs extending radially outward from a proximal end of said slider;
    a plurality of interposing structures extending radially inward from a distal end of said filter housing to block passage of said plurality of tabs thereby in said first direction; and
    a plurality of grooves arranged in a pattern corresponding to locations of tabs within said plurality of tabs, wherein each groove extends between adjacent interposing structures within said plurality of interposing structures, and wherein said plurality of tabs passes through said interposing structures when said plurality of tabs is brought into alignment with said plurality of grooves.

13. The apparatus of claim 12, wherein each interposing structure in said plurality of interposing structures includes a slot extending circumferentially along a distal end of said interposing structure from said groove adjacent said interposing structure, and each tab within said plurality of tabs is movable within said slot of an interposing structure within said plurality of interposers when said filter housing is in said position of maximum extension.

14. The apparatus of claim 11, wherein said filter housing is cylindrical, and wherein said locking means includes:

an external thread extending around said slider adjacent a proximal end of said slider; and an internal thread extending around said filter housing adjacent a distal end of said filter housing, wherein said external and internal threads are in engagement with one another when said slider is in said position of maximum extension from said filter housing.

15. The apparatus of claim 1, wherein said filter housing and said slider permanently enclose said reservoir.

16. The apparatus of claim 1, wherein said filter housing includes a removable end for emptying said reservoir.

* * * * *